United States Patent
Heath et al.

(10) Patent No.: US 10,292,369 B1
(45) Date of Patent: May 21, 2019

(54) NON-CONTACT DETECTION OF PHYSIOLOGICAL CHARACTERISTICS OF EXPERIMENTAL ANIMALS

(71) Applicant: Vium, Inc., San Mateo, CA (US)

(72) Inventors: Kyle Howard Heath, Menlo Park, CA (US); Jonathan Noble Betts-Lacroix, Belmont, CA (US)

(73) Assignee: Vium, Inc., San Mateo, CA (US)

( * ) Notice: Subject to any disclaimer, the term of this patent is extended or adjusted under 35 U.S.C. 154(b) by 197 days.

(21) Appl. No.: 14/788,749

(22) Filed: Jun. 30, 2015

(51) Int. Cl.
| | | |
|---|---|---|
| *A01K 29/00* | (2006.01) | |
| *A61B 5/08* | (2006.01) | |
| *A61B 5/00* | (2006.01) | |
| *A61B 5/087* | (2006.01) | |

(52) U.S. Cl.
CPC .......... *A01K 29/005* (2013.01); *A61B 5/0077* (2013.01); *A61B 5/0816* (2013.01); *A61B 5/0873* (2013.01); *A61B 5/7203* (2013.01); *A61B 5/7246* (2013.01); *A61B 5/7278* (2013.01); *A61B 5/7485* (2013.01); *A61B 2503/40* (2013.01); *A61B 2503/42* (2013.01); *A61B 2576/00* (2013.01)

(58) Field of Classification Search
CPC .. A01K 29/005; A61B 5/0816; A61B 5/0873; A61B 5/7485
See application file for complete search history.

(56) References Cited

U.S. PATENT DOCUMENTS

| | | | |
|---|---|---|---|
| 4,845,887 A | 7/1989 | Snyder | |
| 5,963,664 A * | 10/1999 | Kumar | G06K 9/32 348/47 |
| 6,053,738 A | 4/2000 | Ivey, Jr. | |
| 6,231,032 B1 | 5/2001 | Ivey, Jr. | |
| 7,718,119 B2 | 5/2010 | Tajima | |
| 7,882,135 B2 | 2/2011 | Brunner et al. | |
| 8,149,273 B2 | 4/2012 | Liu et al. | |
| 8,463,006 B2 | 6/2013 | Prokoski | |
| 8,712,126 B2 | 4/2014 | Piratla et al. | |
| 8,790,269 B2 | 7/2014 | Xu et al. | |
| 2007/0118054 A1 | 5/2007 | Pinhas et al. | |
| 2008/0165861 A1* | 7/2008 | Wen | H04N 19/139 375/240.26 |

(Continued)

OTHER PUBLICATIONS

Barron, J.L., et al. "Performance of Optical Flow Techniques." International Journal of Computer Vision 12.1 (1994): 43-77.

(Continued)

*Primary Examiner* — William J Levicky
(74) *Attorney, Agent, or Firm* — Nienstadt PLLC

(57) ABSTRACT

A respiration rate detector is provided for determining a rate of respiration of an experimental animal. The respiration rate detector includes one or more optical detectors to observe an experimental animal and generate a video signal relating to the experimental animal. A controller is provided to process the video signal to determine an optical flow of the video signal and generate an optical-flow signal, and analyze the optical-flow signal to determine the respiration rate of the experimental animal based on a detected repetitive movement of the experimental animal. The respiration rate is thereby detected without requiring physical contact with the experimental animal.

26 Claims, 14 Drawing Sheets

(56) References Cited

U.S. PATENT DOCUMENTS

| | | | |
|---|---|---|---|
| 2011/0112442 A1* | 5/2011 | Meger | A61B 5/0002 600/595 |
| 2011/0288431 A1 | 11/2011 | Alshaer et al. | |
| 2012/0000989 A1 | 1/2012 | Bordier | |
| 2012/0041279 A1 | 2/2012 | Freeman et al. | |
| 2013/0294655 A1* | 11/2013 | Lim | G06T 7/20 382/107 |
| 2014/0223406 A1 | 8/2014 | Teller et al. | |
| 2014/0236036 A1* | 8/2014 | de Haan | A61B 5/1135 600/534 |
| 2014/0253709 A1 | 9/2014 | Bresch et al. | |
| 2015/0103197 A1 | 4/2015 | Djordjevic et al. | |
| 2015/0105670 A1 | 4/2015 | Bresch et al. | |
| 2015/0124067 A1 | 5/2015 | Bala et al. | |
| 2015/0138314 A1 | 5/2015 | Vincent | |
| 2015/0141762 A1 | 5/2015 | Heinrich et al. | |
| 2015/0157270 A1 | 6/2015 | Kyal et al. | |
| 2015/0305657 A1* | 10/2015 | Lasenby | A61B 5/1135 600/476 |
| 2016/0007883 A1* | 1/2016 | Rocque | A61B 5/087 600/407 |

OTHER PUBLICATIONS

Papadakis, N., et al. "Virtual Camera Synthesis for Soccer Game Replays." Journal of Virtual Reality and Broadcasting 9.5 (2012).

Chabout et al, Adult Male Mice Emit Context-Specific Ultrasonic Vocalizations . . . , Jan. 6, 2012, PLoS ONE 7(1): e29401.

Asaba et al., Sexual attractiveness of male chemicals and vocalizations in mice, Aug. 5, 2014, vol. 8, Art. 231, Frontiers in Neurocience.

Tong et al., Properties and mechanisms of olfactory learning and memory, Jul. 7, 2014, vol. 8 Art. 238, Frontiers in Behavioral Neurocience.

Chabout et al., Male mice song syntax depends on social contexts and influences female preferences, Apr. 1, 2015, vol. 9 Art. 76, Frontiers in Behavioral Neurocience.

"Higher Alcanes" Wikipedia Page, accessed May 5, 2015, available at https://en.wikipedia.org/w/index.php?title=Higher_alkanes&oldid=660974133.

Yang et al. Simple Behavioral Assessment of Mouse Olfaction, Jul. 2009, Unit-8.24, Curr Protoc Neurosci.

U.S. Appl. No. 14/549,403, filed Nov. 20, 2014, to Betts-Lacroix et al.

U.S. Appl. No. 14/871,966, filed Sep. 30, 2015, to Betts-Lacroix et al.

U.S. Appl. No. 14/871,986, filed Sep. 30, 2015, to Betts-Lacroix et al.

U.S. Appl. No. 14/871,998, filed Sep. 30, 2015, to Betts-Lacroix et al.

* cited by examiner

NON-CONTACT DETECTION OF PHYSIOLOGICAL CHARACTERISTICS OF EXPERIMENTAL ANIMALS

TECHNICAL FIELD

This application relates to apparatuses and methods for non-contact detection of physiological characteristics of experimental animals.

BACKGROUND

Research is commonly performed on experimental animals that are housed in cages. Typically, these experimental animals are small mammals, such as mice or rats. The research may involve, for example, a drug test, a nutritional test, a genetic test, a test of a surgical procedure, an optogenetics test, or another observation of a physiological or behavioral response to a change in environmental condition or other stimulus. The experimental animals may be divided into a control group and one or more experimental groups. The cages in which the animals are housed may be arrayed in racks.

The housed animals are typically checked in two ways: husbandry checks and experimental checks. Husbandry refers to serving the physiological needs of the animals. Husbandry may include observing the wellbeing of the animals, such as, for example, a health check once or twice a day to make sure that none of the animals has developed any symptoms of disease or has died. Health checks may involve looking at the animals through the transparent cage walls in situ without moving the cages, or alternatively pulling the cages partially or completely out of their racks to visually inspect the animals. Experimental checks, meanwhile, are performed to obtain data for the research being conducted. Experimental checks may involve closer examination of the animals than husbandry checks, such as involving opening the cages and removing the animals from the cages. Experimental checks may involve, for example, looking for clinical symptoms in the animals. Experimental checks may also include behavioral tests, such as, for example, water maze or hole board tests, extractions of blood or tissue from the animals, or measurements such as imaging of the animals.

However, the data obtained from checking the animals may have limited value. Since human technicians may be needed to perform the checks and the checks may perturb the animals, these checks are performed only at certain times. Thus, the data typically represents only a relatively small set of data points for any given animal.

Furthermore, physically contacting the animals, such as through opening the animals' cages, removing them from their cages, and performing measurements on them—or even just approaching the cage to view the animal through the bidirectionally transparent wall, or partially sliding the cage containing the animal out of a rack—can physiologically or psychologically perturb the animals. The consequences of these types of perturbations are often not well understood. Furthermore, there may be inconsistencies in the perturbations, such as differences in when and how the human technicians perform checks across different individual animals. The animals' physiological states and behavior may therefore be altered in ways that are difficult to predict and inconsistent between distinct animals. Thus, these measurement techniques can interfere significantly with the quality of the data obtained from the experiment.

The process of checking the experimental animals may also cause contamination of the animal's living space or the testing equipment. This contamination may, in turn, exacerbate the differences in conditions under which the animals are housed. For example, one human technician may introduce one particular foreign odor into one living space, while another human technician introduces a different odor into another living space. The human technicians who are handling animals from different cages, or using common equipment, may also cause cross-contamination between animals in different cages.

In addition, a substantial amount of resources, such as the time and labor of skilled technicians, is expended to monitor the animals. This can account for a significant amount of the total cost of running such an experiment.

Thus, it is desirable to perform checks on experimental animals in a way that yields high-resolution and reliable data in relation to the number of animals. It is also desirable to avoid physical contact with the animals, inconsistent perturbations of the animals, and cross-contamination between animals in different cages when the animals are checked. Moreover, it is desirable to reduce the amount of time and labor that is expended on running the animal experiment.

SUMMARY

In one embodiment, a respiration rate detector is provided for determining a rate of respiration of an experimental animal. The respiration rate detector comprises one or more optical detectors to observe an experimental animal and generate a video signal relating to the experimental animal. A controller processes the video signal to determine an optical flow of the video signal and generate an optical-flow signal, and analyzes the optical-flow signal to determine the respiration rate of the experimental animal based on a detected repetitive movement of the experimental animal. The respiration rate is detected without requiring physical contact with the experimental animal.

In another embodiment, a method of determining a rate of respiration of an experimental animal is provided. The method comprises observing an experimental animal with one or more optical detectors to generate a video signal and processing the video signal to determine an optical flow of the video signal and generate an optical-flow signal. The optical-flow signal is analyzed to determine the respiration rate of the experimental animal based on a detected repetitive movement of the experimental animal. The respiration rate is detected without requiring physical contact with the experimental animal.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and aspects of the transmission electron microscopes described herein and, together with the description, serve to explain the principles of the invention.

DETAILED DESCRIPTION

An electronic monitor may be adapted to be removably coupled to a cage housing experimental animals to be positioned in a predefined position relative to the cage and monitor one or more of the experimental animals. The electronic monitor can be adapted to maintain a substantially sterile barrier between the animal living space in the cage and the environment external to the cage while the electronic monitor is coupled to the cage. Sterility refers to chemical and biological isolation from the ambient environment, such as, for example, isolation from foreign odors, soot particles, viruses, parasitic worm eggs, bacteria, prions, proteins, metabolites, parasitic mites and their eggs, and humidity and temperature fluctuations. The electronic monitor can thereby monitor the experimental animals while minimizing perturbations to the animals. Examples of such an electronic monitor are described in U.S. patent application Ser. No. 14/549,403 to Betts-LaCroix et al., which is incorporated herein by reference in its entirety.

Figure 1A:
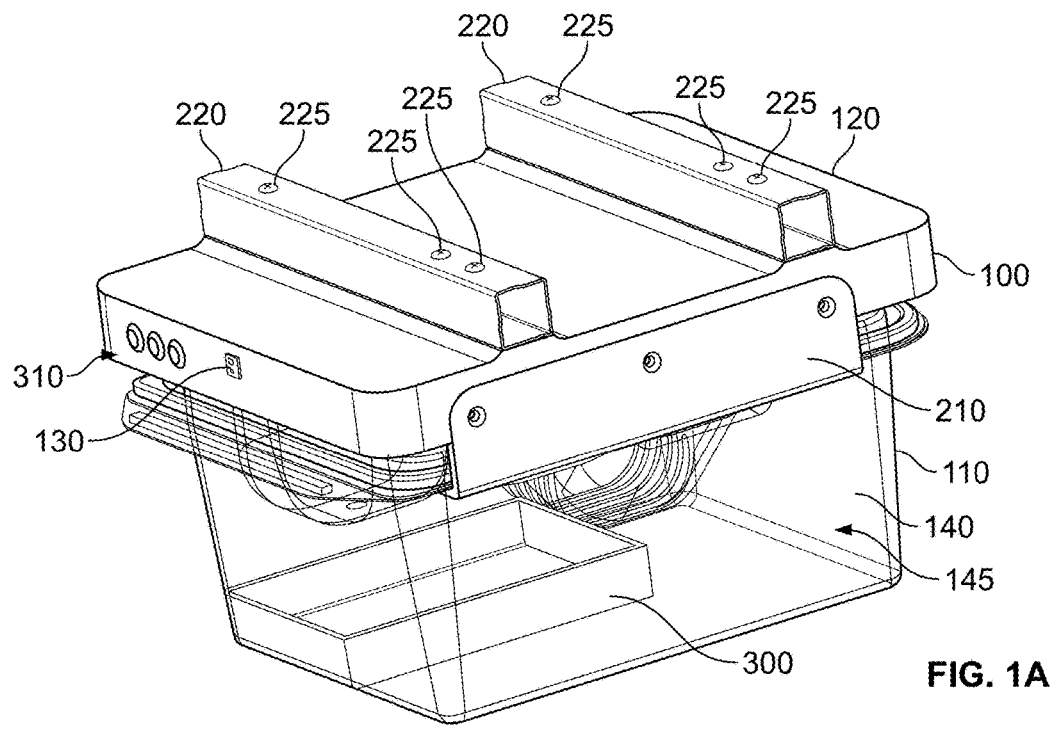
FIGS. 1A and 1B are three-dimensional perspective views of line drawings of an example of an embodiment of an electronic monitor that is coupled to a cage.
Figure 1B:
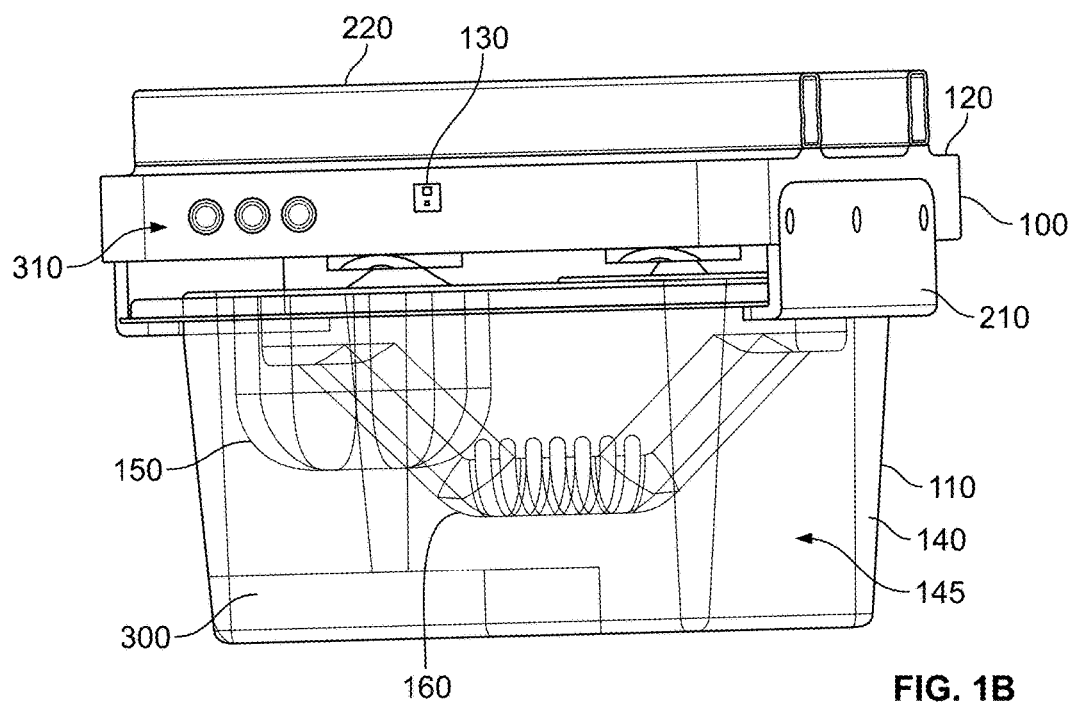

FIGS. 1A and 1B illustrate an example of an embodiment of an electronic monitor 100 and a cage 110 that are mechanically coupled to each other. Electronic monitor 100 has a housing 120 to which electronic and/or other components of electronic monitor 100 are attached. Housing 120 may form a substantially airtight enclosure around sensitive components of electronic monitor 100. These sensitive components may include, for example, cameras, microphones, electromagnetic sources, electronic circuitry, and optical components such as fiber optics. For example, housing 120 may include one or more seals or gaskets to be capable of maintaining an airtight environment around the key or sensitive components of electronic monitor 100. Electronic monitor 100 may also have one or more ambient sensors 130 to determine characteristics of the environment outside cage 110. Ambient sensors 130 may determine, for example, an outside light level or temperature, or to detect ambient sound.

Cage 110 has one or more walls 140 that enclose living space 145 of the experimental animals. In one embodiment, walls 140 define a living space 145 that is approximately a rectangular prism. In other embodiments, however, walls 140 may have other shapes or dimensions. In illustrative examples, a mouse cage may be shaped and sized to house from one to about five mice, while a rat cage may be capable of housing up to about 10 mice. For example, mice may be housed singly or in pairs. In one embodiment, walls 140 of cage 110 enclose a substantially cuboid living space 145 of at least 10 cm×10 cm×5 cm.

Cage 110 may also include shaped features to provide water and/or food to the experimental animals. For example, cage 110 may have a water dispenser 150. Cage 110 may also have a food dispenser 160. If cage 110 is of a disposable type, then water dispenser 150 and/or food dispenser 160 may be pre-filled with an amount of water or food corresponding to an expected lifespan of the animals, an expected timespan of an experiment, or a given interval between cage changes. A given interval between cage changes may be, for example, one, two, or four weeks, such as may be suitable for the particular types of cage, animal, and experiment.

Figure 2A:
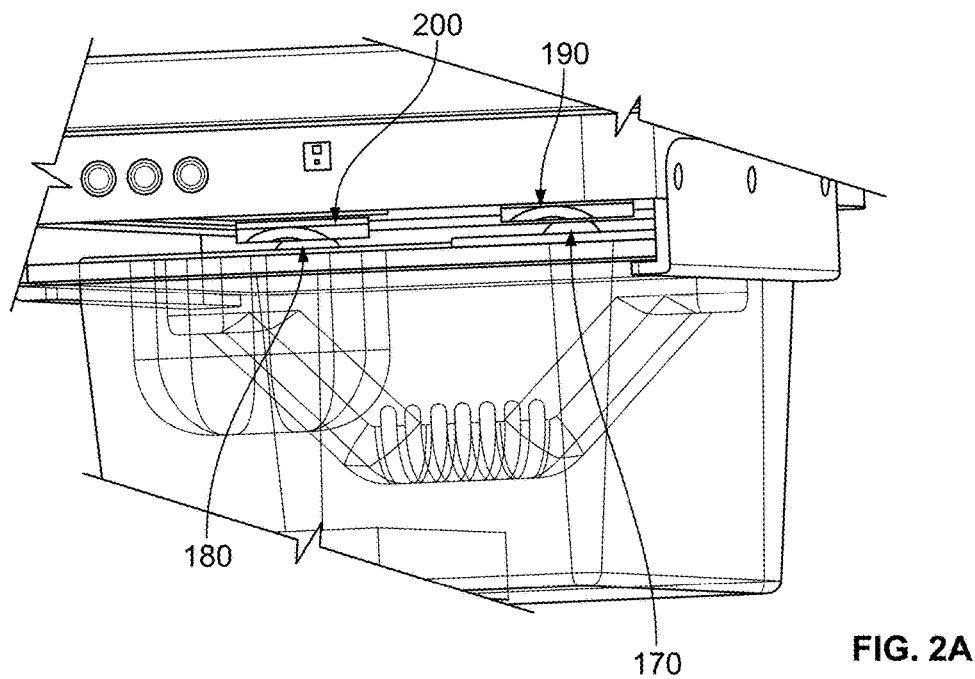
FIGS. 2A and 2B are three-dimensional perspective views of line drawings of the example of the electronic monitor coupled to the cage that is illustrated in FIGS. 1A and 1B.
Figure 2B:
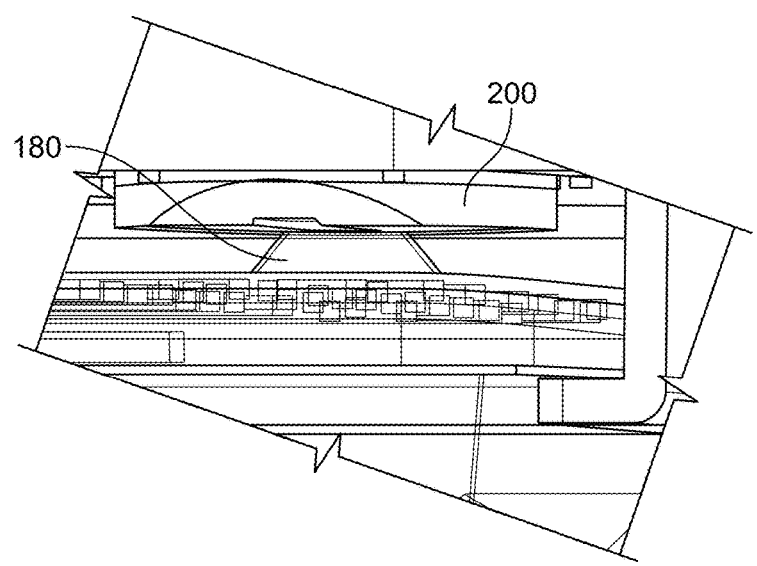

Cage 110 may include at least one air inlet for clean air, and at least one air outlet for contaminated air. In one example, illustrated in FIGS. 2A and 2B, cage 110 has air nipples 170, 180 that structurally complement air inlet 190 and air outlet 200, respectively. Air inlet 190 and air outlet 200 may couple to an external air supply conduit and an air exhaust conduit, respectively.

Electronic monitors 100 may be structurally adapted to permit easy and fast uncoupling of cages 110 from electronic monitors 100 by a human technician or even by a robot. For example, electronic monitors 100 may be structurally adapted to permit coupling and uncoupling by sliding cages 110 into and out of electronic monitors 100. Returning to FIGS. 1A and 1B, in one version, electronic monitors 100 have arms 210 extending from housing 120 to support cages 110, such as for example L-shaped arms 210 extending from under housing 120 to stably hold cages 110 underneath housing 120. Furthermore, when a cage 110 is slid into electronic monitor 100, air nipples 170, 180 may mechanically snap into air inlet 190 and air outlet 200, respectively, to create substantially sealed air channels and hold cage 110 in place with respect to electronic monitor 100.

Multiple cages 110 that are coupled to respective electronic monitors 100 may be mechanically supported in arrays by a rack. Cages 110 may be supported by the rack by nonpermanent mechanical coupling, such that they can be easily removed from the rack if desired. For example, electronic monitors 100 may be supported by mounting rails 220 of the rack to stably hang electronic monitors 100 from the rack (or, in alternative versions that are not illustrated here, electronic monitors 100 may attach to mounting rails 220 from a side of electronic monitors 100 or even underneath cage 110). Electronic monitors 100, in this example, may be attached to mounting rails 220 of the rack by bolts 225 that pass through holes in rails 220.

The rack may also structurally provide one or more resources used in the cage, such as, for example, conveying clean air and exhausting used air, electrical power, electrical or optical signals, water, and nutrients for the experimental animals. For example, an air supply conduit and an air exhaust conduit adapted attach to cage 110 may extend from the cage rack or even constitute part of the rack itself. Similarly, electrical wiring for power and transmission of signals may be extended inside or along the beams of the rack and connect to electronic monitors 100, such as via complementary ports, for example through respective "male" and "female" connectors, on electronic monitors 100 and the rack.

Figure 3:
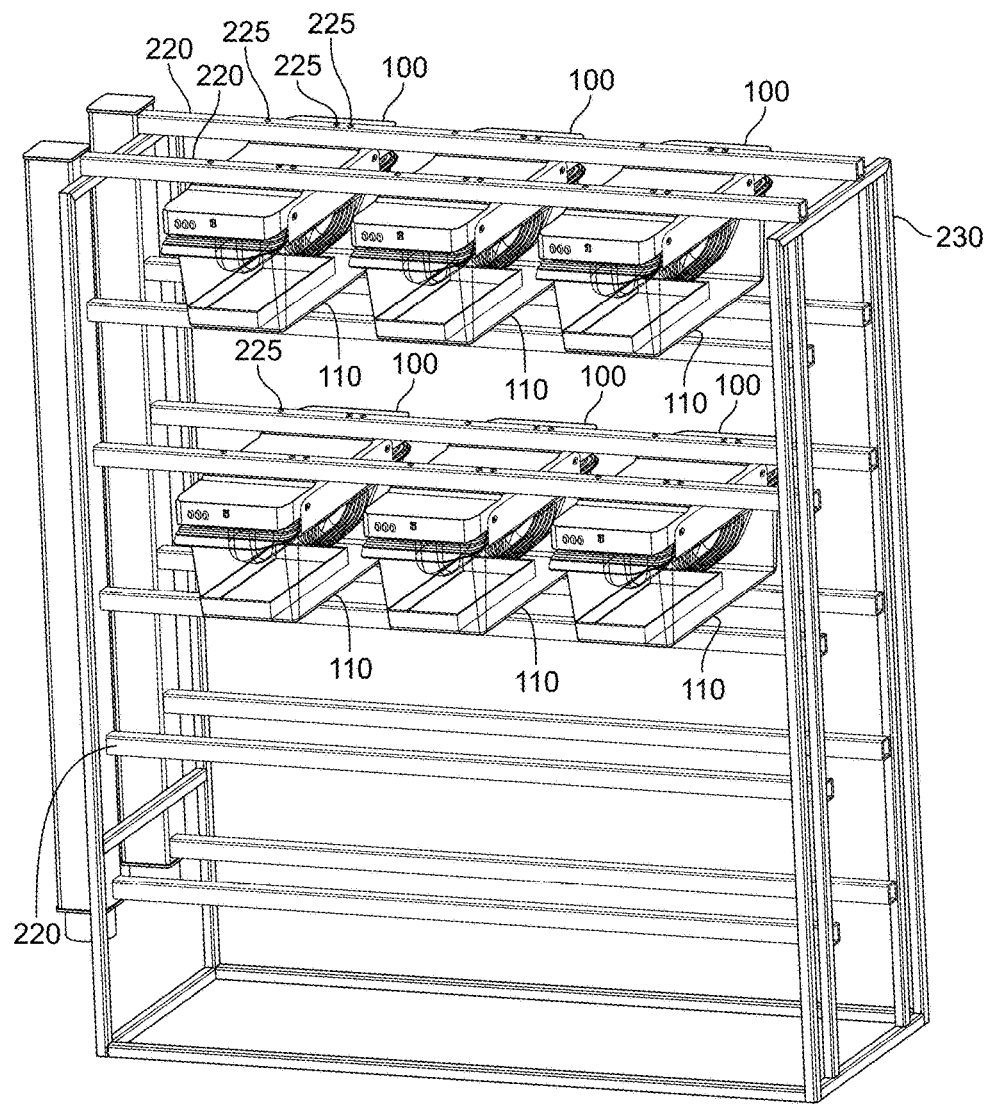
FIG. 3 is a three-dimensional perspective view of an example of an embodiment of a rack having multiple electronic monitors coupled to respective cages and arranged in a two-dimensional rectilinear grid array.

In certain embodiments, the rack supports the cages in a two-dimensional or three-dimensional rectilinear grid array. FIG. 3 illustrates an example of an embodiment of a rack 230 that supports multiple cages 110 coupled to respective electronic monitors 100, which are arranged in the rack in a two-dimensional rectilinear grid array. However, racks may be implemented that support other suitable assemblages of cages 110. For example, a rack may be adapted to allow cages 110 to be stacked in a rotatable cylindrical array. In other examples, the rack may be adapted to stack cages 110 in hexagonal, diagonal, or other configurations.

Figure 4:
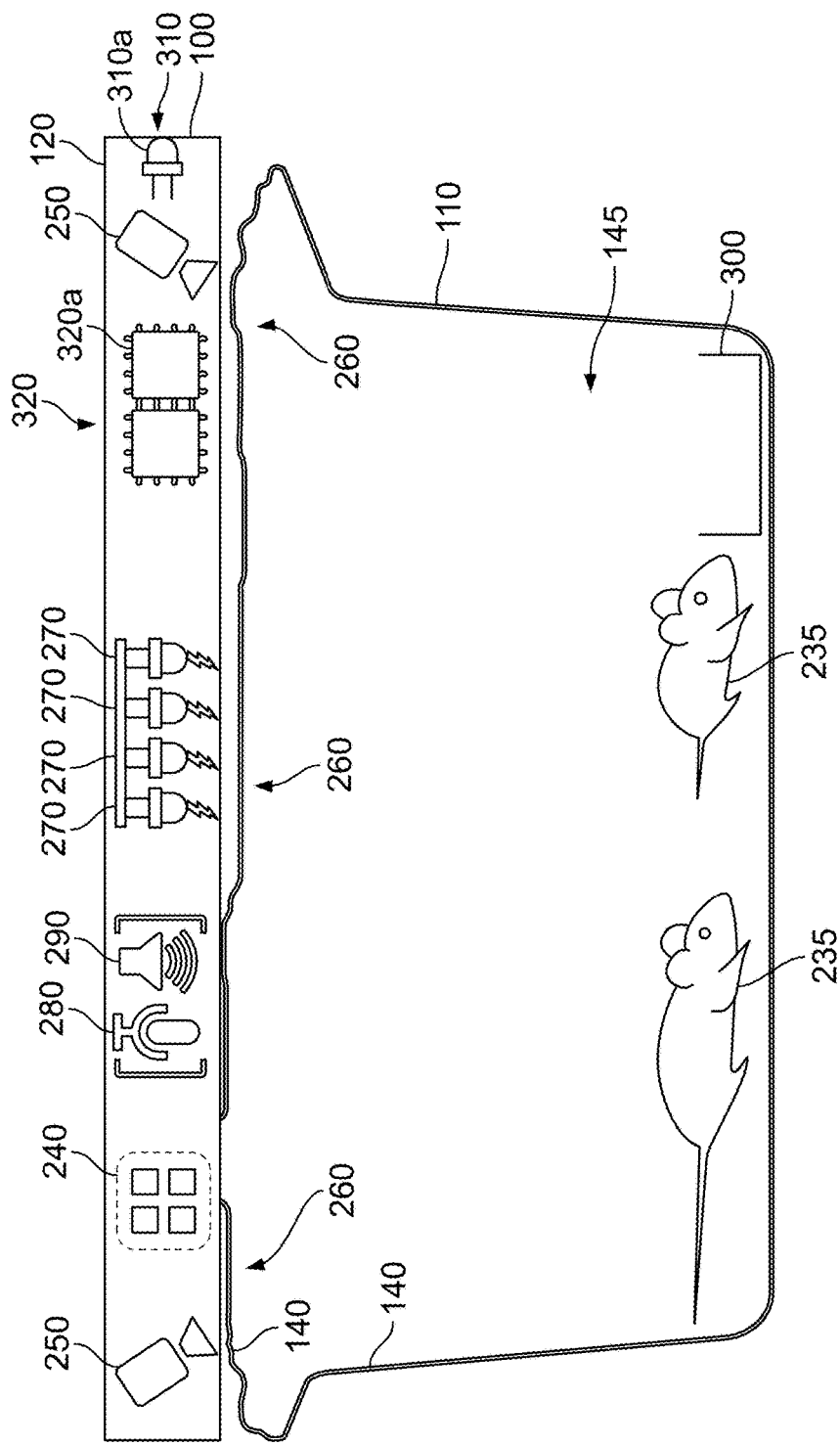
FIG. 4 is a schematic illustration side view of an example of an embodiment of an electronic monitor coupled to a cage.

FIG. 4 is a schematic illustration of a side view of an example of an embodiment of an electronic monitor 100 coupled to a cage 110 that houses experimental animals 235. Electronic monitors 100 may permit high-resolution and reliable data to be collected on the experimental animals while substantially avoiding inconsistent perturbations of the animals or cross-contamination between animals. And, electronic monitors 100 may be able to provide these advantages without substantially interfering with other aspects of conventional animal husbandry workflows. Electronic monitors 100 may thus be incorporated into an existing animal husbandry workflow without requiring revamping of various aspects of the workflow, such as technician training and existing equipment.

Electronic monitor 100 may include one or more atmospheric sensors 240 to detect one or more atmospheric conditions inside cage 110. Sensors 240 may include, for example, a humidity sensor to detect water vapor. The humidity sensor can be used, for example, to detect whether the cage has undesirably flooded with water or another liquid. Sensors 240 may also include sensors to detect percentage levels of various gases. For example, sensors 240 may include an ammonia sensor to detect a level of ammonia ($NH_3$) in the atmosphere of cage 110. A level of ammonia that is above a particular level may indicate an undesirably high level of waste of the experimental animals, for example, and therefore a desirability of replacing the flooring or bedding, moving the animals to another cage, or cleaning the cage. Sensors 240 may additionally include a carbon monoxide sensor to detect a level of carbon monoxide (CO) in the cage, a nitrogen dioxide sensor to detect a level of nitrogen dioxide ($NO_2$) in the cage, one or more sensors for a preselected group of oxidizing gases, and/or one or more sensors for a preselected group of reducing gases. Furthermore, sensors 240 may include a temperature sensor to detect a temperature inside the cage. Atmospheric sensors 240 may be disposed in contact with air coming out of cage 110, such as in the path of the air outlet, to avoid contamination of the inside of cage 110 while obtaining a desirably accurate reading of current atmospheric conditions inside cage 110.

The electronic components of electronic monitor 100 may also include one or more electromagnetic detectors 250, such as shown in the example of FIG. 4. Detectors 250 may be coupled to housing 120 at predefined positions. For example, these predefined positions may have a line-of-sight through one or more signal-interface sections 260 and into living space 145 of cage 110 when electronic monitor 100 is coupled to cage 110. The "line-of-sight" refers to a possible path of propagation of electromagnetic radiation that is suitably transparent for detection of the electromagnetic radiation by detectors 250. The path of propagation may either form a substantially straight line or change direction one or more times (the latter type being referred to here as an "indirect" line-of-sight). Electromagnetic detector 250 may thereby be adapted to detect electromagnetic radiation that is transmitted through signal-interface sections 260. In one example, one or more of electromagnetic detectors 250 has an indirect line-of-slight through section-interface section 260 into living space 145 of cage 110, such as shown in the example of FIG. 4. Furthermore, if housing 120 has a substantially airtight enclosure, the substantially airtight enclosure may be designed to contain electromagnetic detectors 250 therein to protect electromagnetic detectors 250 from dirtying or damage by the outside environment.

The electromagnetic detectors of the electronic monitor may include one or more cameras. The cameras may be able to capture video or, in other cases, still images. The optics of the cameras may be, for example, conventional camera optics, light-field camera optics, or structure-of-light camera optics. Furthermore, the cameras may be adapted to capture images in any suitable range of wavelengths, such as, for example, the visible spectrum, near infrared range, or far infrared range. For example, a camera may be adapted to detect radiation in the far infrared range to generate a signal that electronic monitor 100 uses to determine temperatures in cage 110.

The camera may be adapted to capture multiple different images of the space inside the cage, such as substantially the same area inside the cage, which can be processed together to enhance the data richness, such as the image resolution, of the observed area. For example, two or more such images may be digitally processed to deconvolve scratches and/or other imperfections in the transparency of the cage from the image. In one exemplary embodiment, the camera is adapted to be repeatedly physically shifted between at least two predefined positions in order to capture respective images from at least two different perspectives. Alternatively, the camera could be held still while a mirror or other optical device is physically shifted between at least two predefined positions in order to capture the images from the two or more optical perspectives. Alternatively or in addition, the camera may be a light-field camera that is adapted to capture two or more images simultaneously at different focus levels. In yet another embodiment, two or more fixed cameras may be positioned next to each other to simultaneously capture two or more images of substantially the same area from slightly different perspectives.

Electronic monitor 100 may also have one or more electromagnetic sources 270, which may be coupled to housing 120 at a predefined position that has a line-of-sight into living space 145 of cage 110, such as through signal-interface section 260. Sources 270 may be adapted, in one embodiment, to illuminate one or more desired areas of living space 145 to enhance detection by electromagnetic detectors 250. For example, one of sources 270 may illuminate an area of living space 145 with light at one or more wavelengths that are selected to reduce or minimize perturbation of experimental animals 235, and the illuminated area of living space 145 may be observed via one of electromagnetic detectors 250 that is adapted to detect light at those preselected wavelengths.

Housing 120 of electronic monitor 100 may have a substantially flat wall of one of walls 140 that is adapted to, when electronic monitor 100 is coupled to cage 110, be positioned approximately adjacent to signal-interface section 260 of cage 110. For example, if cage 110 is mounted directly underneath electronic monitor 100, such as shown in the examples of FIGS. 1A, 1B, and 3, then signal-interface section 260 may be located in a top wall of cage 110. In one version, cage 110 is disposable between cycles of housing a set of experimental animals. In one version, signal-interface section 260 may be any substantially transparent area of walls 140 of cage 110.

Electronic monitor 100 may further include one or more acoustic sensors 280, such as microphones, to capture sounds from inside cage 110. Acoustic sensors 280 may be adapted to capture sounds in any suitable range of frequencies, such as, for example, in an infrasonic, human-audible, or ultrasonic range. Acoustic sensors 280 may be adapted to capture sounds in the range of from about 0 Hz to about 100 kHz. In one example, acoustic sensors 280 may be adapted to capture sounds in the range of from about 15 kHz to about 35 kHz to listen to mouse vocalizations. In another example, acoustic sensors 280 may be adapted to listen for predefined distinctive sounds made by experimental animals under known conditions.

Furthermore, electronic monitor 100 may have acoustic emitters 290 to transmit sounds into cage 110. In one version, acoustic emitters 290 transmit one or more sounds into living space 145 that are stimuli to observe a response, or obtain a predicted response, from the experimental animals. These acoustic stimuli may be part of the overall experiment being performed on the animals, for example. The acoustic stimuli may, for example, simulate noises created by the same type of experimental animals. Alternatively or in addition, acoustic emitters 290 may be used in a noise-canceling mode to substantially cancel out unwanted noises created in the environment outside cage 110. These may include, for example, loud or sudden noises by nearby laboratory staff, equipment, or animals in other cages that may otherwise perturb the experimental animals.

In one version, a weight scale 300 is provided inside the cage to measure the mass of an experimental animal. Weight scale 300 may transmit the measured mass data to electronic monitor 100 by electromagnetic transmission that does not substantially affect the sterility barrier between living space 145 in cage 110 and electronic monitor 100. For example, weight scale 300 may transmit the measured mass information to electronic monitor 100 by a modulated near-infrared beam or radio frequency (RF) signal. Weight scale 300 may be located in living space 145 where an experimental animal can identifiably or predictably stand on scale 300.

Electronic monitor 100 may also include one or more user interfaces 310 to display information to a human supervisor or receive one or more inputs from the human supervisor. The human supervisor may be, for example, an animal-husbandry technician who is responsible for the physiological and psychological condition of the animals, a scientist who is conducting the experiment on the animals, or another kind of human analyst. One or more of user interfaces 310 may be adapted to display a compilation of information received from electronic monitors 100 at individual housings 110 of electronic monitors 100, at the level of the rack (such as rack 230 shown in FIG. 3), or at client devices such as personal computers or handheld devices. The compilation may be, for example, a summary or parallelized display of information derived from electronic monitors 100. The presented information may include one or more of raw data from ambient sensors 130 of electronic monitors 100, raw data from atmospheric sensors 240, raw data from electromagnetic detectors 250, raw data from acoustic sensors 280, raw data from weight scales 300 inside cages 110, and information resulting from processing of such raw data by one or more of controllers 320. For example, user interfaces 310 may be adapted to display a plurality of metrics to the human supervisor as a guide, receive an input relating to one or more of the metrics from the human supervisor, and navigate through raw data associated with the metrics based on the human input. For example, the human input may be associated with a status of experimental animals 235.

Certain user interfaces 310a may be disposed on housing 120 of electronic monitor 100 itself, or, additionally or alternatively, at one or more remote locations. User interfaces 310 may include, for example, one or more light-emitting diodes (LEDs) (such as shown in FIG. 4 by user interface 310a), two-dimensional color displays, or acoustic speakers.

Electronic monitors 100 may also include at least one controller 320 to control the operation of electronic monitors 100, control user interfaces 310 to interface with a human supervisor, and/or interface with an external server or network. Controller 320 may automatically control one or more aspects of operation of electronic monitor 100, and may be adapted to largely or wholly automate the operation of electronic monitor 100. The controller may, for example, receive inputs from a human user, provide instructions to other components of monitor 100, perform processing of data received from ambient sensors 130, atmospheric sensors 240, electromagnetic detectors 250, acoustic sensors 280, and weight scale 300, and/or output signals, such as alerts or other indicators. Controller 320 may be adapted, for example, to receive signals from ambient sensors 130, atmospheric sensors 240, electromagnetic detectors 250, acoustic sensors 280, and weight scale 300, and to transmit control signals to electromagnetic sources 270 to provide electromagnetic radiation into living space 145, or to transmit signals to acoustic emitters 290, or to transmit signals to user interfaces 310.

Controller 320 may include one or more microprocessors, controllers, processing systems, computers, and/or circuitry, such as any combination of hardware or software modules.

Components of the controller may be distributed across one or more different physical locations and these components may communicate with each other to perform the operations of the controller. For example, components of controller 320 may be physically located at the individual electronic monitors 100, such as at the level of rack 230 (e.g., connected to rack-level data input and output ports), and/or at remote client devices such as personal computers or handheld devices.

Controller 320 may be implemented in any quantity of hardware components, such as including Raspberry Pi, an integrated circuit such as, for example, an application-specific integrated circuit (ASIC), field-programmable gate array (FPGA), or "system on a chip" (SoC), and/or other processor, memory, bus, input/output, or communications systems. Furthermore, some or all of these hardware components may be located locally or remotely. For example, controller 320 may be implemented partially or entirely through cloud computing. Controller 320 may operate any commercially available operating system software, including, for example, Linux, Windows, MacOS, iOS, Android, Unix, OS/2, or any other commercially available and/or custom software. For example, controller 320 may operate customized animal-monitoring and signal-processing software. Furthermore, controller 320 may include one or more types of input devices, such as for example a touchpad, keyboard, button panel, mouse, microphone, or voice recognition device.

Controller 320 may be adapted to process received data and/or human inputs to determine values of one or more metrics relating to experimental animals 235 or living space 145. The metrics may include one or more physiological, behavioral, or environmental metrics. Physiological metrics may include, for example, respiration rate, health check, heart rate, body weight, thinness, body temperature, metabolism, coat characteristics such as rough hair coat, stress level, a Body Condition Score ("BCS"), alopecia, whether the animal is dead, ataxia or another central nervous system (CNS) disorder, circling or head tilt, dehydration, dermatitis, distended abdomen, dyspnea, dystocia, ear problems, emaciation, eye problems, fight wounds, hunched posture, hydrocephalus, irregular gait, lesions, lethargy, listlessness, malocclusion, necropsy, the number of animals in a cage, paleness of color, the presence of post-operative staples, prolapse, pruritus, seizure, other sickness, or the presence of a tumor. Behavioral metrics may include, for example, activity states and patterns, food and water consumption by the experimental animals, whether an animal appears to be missing from a particular region or the entire cage, a sleep or awake state, an animal biting itself, an animal biting its tail, a caught or trapped state of an animal, contact between animals, defecation, urination, drinking, eating, exercise, foraging, grooming, a hunched posture, inactivity, nose-poking, rearing up, running, repetitive behavior, licking, scratching, fighting, wincing, and sociability. Environmental metrics may include, for example, an amount of water or food remaining for consumption by the animals in a cage, high or low humidity, high or low ammonia level, high or low environmental temperature, illumination level, an ajar state or equipment, a broken state of equipment, a slotted or unslotted state of the cage, an open state of the cage, a change in bedding, a fill-up of food or water, maximum or minimum humidity for a rack containing the cage, maximum or minimum temperature for a rack containing the cage, and general cage or rack problems.

Controller 320 may present one or more of the monitored metrics on one or more of user interfaces 310 for observation by a human supervisor. In one version, the monitored metrics are displayed to the human supervisor in a "fused" manner. This means that the monitored metrics are displayed or otherwise presented to the human supervisor in a compact or ergonomic manner that overlays, joins, or compares a plurality of metrics that are being, or have been, monitored. For example, temperatures or measurements of activity in different cages may be overlapped in the same plot for ready visual comparison by the human supervisor. This may allow the human supervisor to efficiently or ergonomically observe the conditions in different cages, or evaluate the conditions in a particular cage of interest relative to other cages.

Multiple animals that are under the same experimental conditions may be selected to be housed in the same cage. For example, animals in a control group may be housed together, while animals in a particular experimental group may be housed together. When animals that are under the same experimental conditions are housed in the same cage, it may not be necessary for electronic monitor 100 to track the individual identities of the animals. Rather, since the mice may be treated as experimentally identical, aggregated or averaged information relating to all of the mice in a particular cage may suffice for purposes of the experiment.

Controller 320 may be adapted to process one or more input signals received from the human supervisor through one or more of user interfaces 310 as inputs to a machine learning algorithm that is executed by controller 320. For example, controller 320 may display to the human supervisor, via one of user interfaces 310, a condition inside the cage, such as a predicted status of an experimental animal. This may be referred to as a "state signal." The predicted status of an experimental animal may be, in one example, that the animal is healthy or sick. Controller 320 may simultaneously display a level of confidence that controller 320 has in its prediction or estimation of the condition. The human supervisor may observe the experimental animal, either remotely through the user interface or in person, and confirm or reject the prediction. Alternatively or in addition to confirmations and rejections, the human supervisor may provide feedback by setting parameters under which controller 320 predicts the condition. Based on this repeated feedback from the human supervisor, controller 320 may automatically learn to associate a received signal with a particular condition.

In addition to obviating direct, physical human interaction, electronic monitors 100 can couple to cages 110 in a manner that does not otherwise interfere with the experimental animals. For example, electronic monitors 100 may obviate a need to surgically implant or otherwise insert any sensor, needle, or other device into the body of an experimental animal or to tether the experimental animal in any way. Furthermore, by coupling to cages 110 that are substantially closed from all sides, electronic monitors 100 may be capable of handling husbandry and experimental tasks without placing detectors 250 or sensors 280 in contact with the atmosphere of the living space 145 of the experimental animals.

Controller 320 may control electromagnetic detectors 250, and optionally also electromagnetic sources 270, to determine the respiration rate of one or more of the experimental animals by optical methods and devices without requiring physical contact with the animals that could perturb them. These optical methods and devices may also be substantially insusceptible to acoustic conditions inside or outside of the cage.

Electromagnetic detectors 250 and/or electromagnetic sources 270 may be used to observe the experimental animals using light in the visual spectrum in one version. In another version, however, electromagnetic detectors 250 and/or electromagnetic sources 270 may use infrared light or one or more wavelengths of light that are substantially invisible to the experimental animals. For example, in one embodiment electromagnetic detectors 250 may detect ambient light in the visual spectrum during daytime hours and invisible light such as in the infrared spectrum during nighttime hours. These wavelengths of light used may be selected in part based on the normal behavioral characteristics of the animals, such as whether the experimental animals are diurnal or nocturnal.

Controller 320 may receive a time sequence of images (which can be referred to as "frames" of a video) of an experimental animal from electromagnetic detectors 250. The images may be of a resolution that is selected to be suitably high that changes in the image corresponding to respiration of the experimental animal are detectable. In one example embodiment, each of the images is a two-dimensional color image. Controller 320 may apply one or more calibrations or corrections to the image, such as for example a geometric camera calibration to correct lens distortion.

Figure 5A:
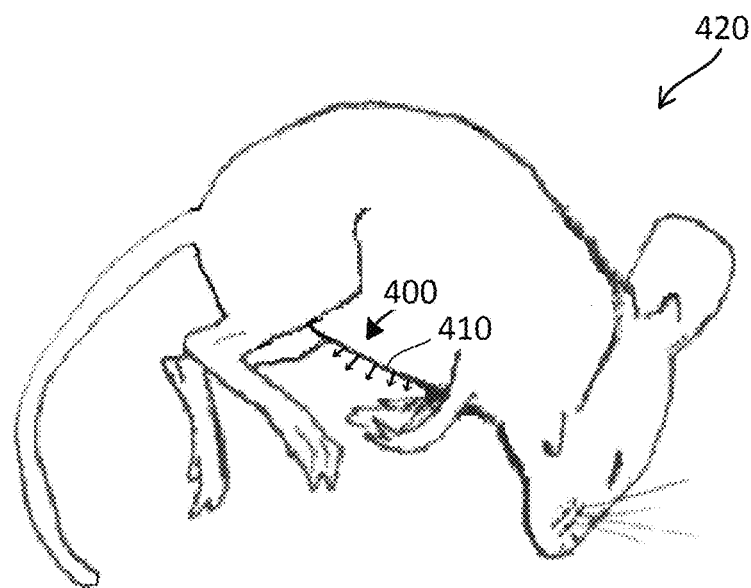
FIGS. 5A and 5B are schematic illustrations of an example of an embodiment of motion vectors for flank movement of a mouse that corresponds to the respiration of the mouse.
Figure 5B:
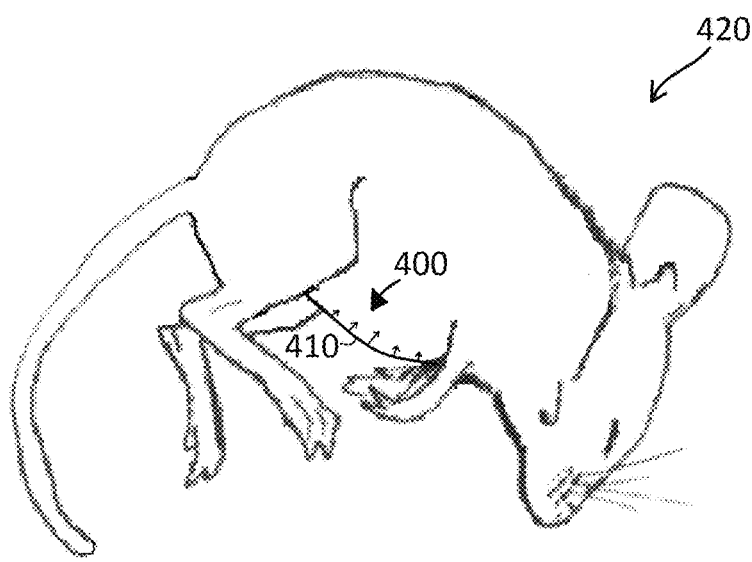

Controller 320 process the video from electromagnetic detectors 250 to analyze displacements of the body of the experimental animal. For example, controller 320 may measure a movement of a flank of the experimental animal. In other example embodiments, however, a movement of a top (dorsal) or bottom (ventral) surface of the experimental animal is measured. FIGS. 5A and 5B are schematic illustrations of an example of an embodiment of motion vectors 400 for movement of a flank 410 of a mouse 420 that corresponds to the respiration of the mouse. In these figures, the motion vectors are exaggerated for the sake of illustration.

In one version, images from multiple electromagnetic detectors 250 corresponding to different perspectives into the living space of the experimental animals are synthesized to generate a single image with better visibility of the experimental animals, such as the entire cage floor that can be traversed by the animals. For example, these multiple images may have been captured at substantially the same point in time to generate a synthesized image for that time point. The synthesized images may then form a synthesized video composed of a time sequence of the synthesized images as frames. This may avoid occlusions that are not present from one or more of the detector perspectives and improve the accuracy of imaging.

Controller 320 may use a homography to project the images onto a plane corresponding to the cage floor as part of generating the synthesized image. For example, the projected views may be fused into a synthetic overhead view of the cage floor, where the electromagnetic detector (e.g., camera) chosen for certain pixel information in the synthetic view is selected to reduce occlusions and maximize sensing resolution. Generating a synthesized image may facilitate setting parameters in terms of physically meaningful or intuitive dimensions.

Figure 6A:
FIGS. 6A and 6B are example of embodiments of grayscale images of two separate mice in the same cage taken by different respective cameras from different respective viewpoints.
Figure 6B:

FIGS. 6A and 6B are example of embodiments of grayscale images of two separate mice in the same cage taken by different respective cameras from different respective viewpoints. FIG. 7A is a grayscale image that has been generated by synthesizing two images of the mice in FIGS. 6A and 6B from the respective cameras used to capture the images of those figures.

The video frames—whether synthesized or otherwise—may be divided into a tessellation of geometric boundaries that define cells. The tessellation may be a rectilinear grid, for example. Displacements of the cells between sampling times can then be evaluated to determine which displacements correspond to respiration of an experimental animal and the corresponding respiration rate of that animal.

The dimensions and shapes of the cells may be preselected to optimize discrimination of cell displacement (i.e., tracking of a cell across a displacement during a time interval) although the pixel intensities within the displaced cell can change slightly as a result of the movement. In one example, the cell size is chosen so that opposite flanks of the experimental animal fit into different cells; if the cell size were larger, the direction magnitudes could substantially cancel in the vector field for the optical flow. Thus, larger cell sizes may be advantageous for larger animals. On the other hand, if the cell size is too small, the noise floor may be increased, which can make it more difficult to discern the respiration signal. In one version, the cells are defined to have a size of from about 0.001 $cm^2$ to about 400 $cm^2$. In one example, the cells are defined to have a size of from about 0.25 $cm^2$ to about 4 $cm^2$, such as for a mouse or other small rodent.

Controller 320 may process magnitudes and directions of displacements of the cells between sampling times to determine an optical flow of the video signal and output an optical-flow signal that encodes the computed or estimated optical flow. The optical flow may be a representation of movement of patterns in a video between one image frame and another image frame. The optical flow may be described, for example, as a vector field composed of vectors, each vector having a magnitude component and a direction component.

In one embodiment, the vector field representing displacements for each grid cell is encoded by two two-dimensional matrices of floating-point numbers. The optical flow is the displacement of the content of a grid cell between a first time (t_0) and a second time (t_1). The optical flow may be determined by matching the displacement of each of the cells to another set of pixels that is believed to track the physical movement of the feature that was imaged in that cell. In one example, the matching set of pixels is a nearby set of pixels that has the same size as the cell. This matching may be performed at the pixel resolution of the underlying image.

In one embodiment, a correlation method is used for estimating optical flow in which a cell at the first time (t_0) is cross-correlated to its best matching displacement in the two-dimensional image at the second time (t_1) within a predefined search window. However, other suitable matching algorithms may be used. For example, other methods of estimating optical flow include differential methods and energy-based, phase-based, and other region-based techniques.

The matrix pairs may encode the vector field in polar coordinates, where the first matrix encodes a magnitude component of each vector in the vector field while the second matrix encodes a direction component for that vector (e.g., as an angle). Alternatively, the first and second matrices may encode orthogonal components of each vector of the vector field in Cartesian coordinates (i.e., "x" and "y" coordinates).

Figure 7B:
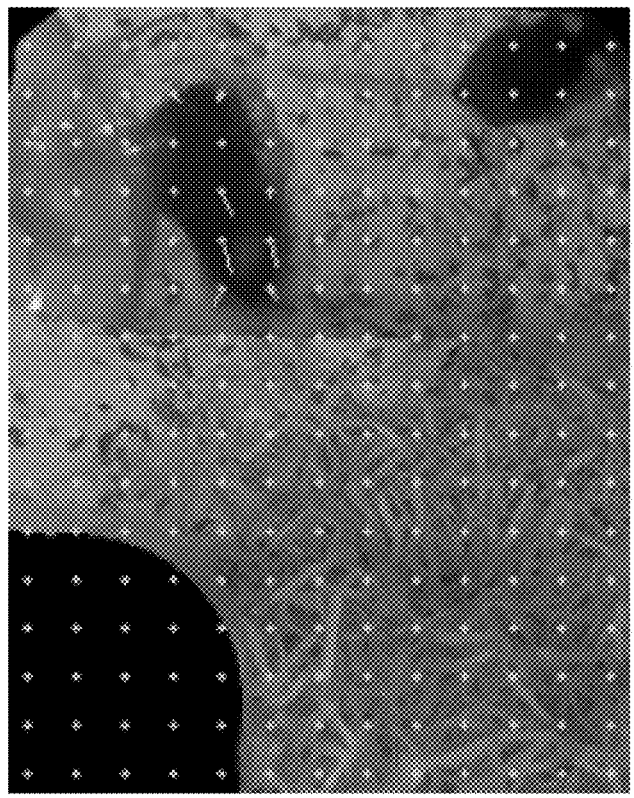
FIG. 7B is the grayscale image of FIG. 7A with an example of an embodiment of a vector field representing optical flow overlaid on the image
Figure 7A:
FIG. 7A is a grayscale image that has been generated by synthesizing two images of the mice in FIGS. 6A and 6B from the respective cameras used to capture the images of those figures.
Figure 8:
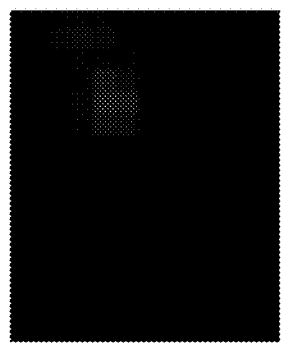
FIG. 8 is a pixelated representation of the magnitude component of the vector field shown in FIG. 7B across differential spatial cells.

FIG. 7B is the grayscale image of FIG. 7A with an example of an embodiment of a vector field representing optical flow overlaid on the image. FIG. 8 is a pixelated representation of the magnitude component of the vector field shown in FIG. 7B across differential spatial cells.

Figure 9:
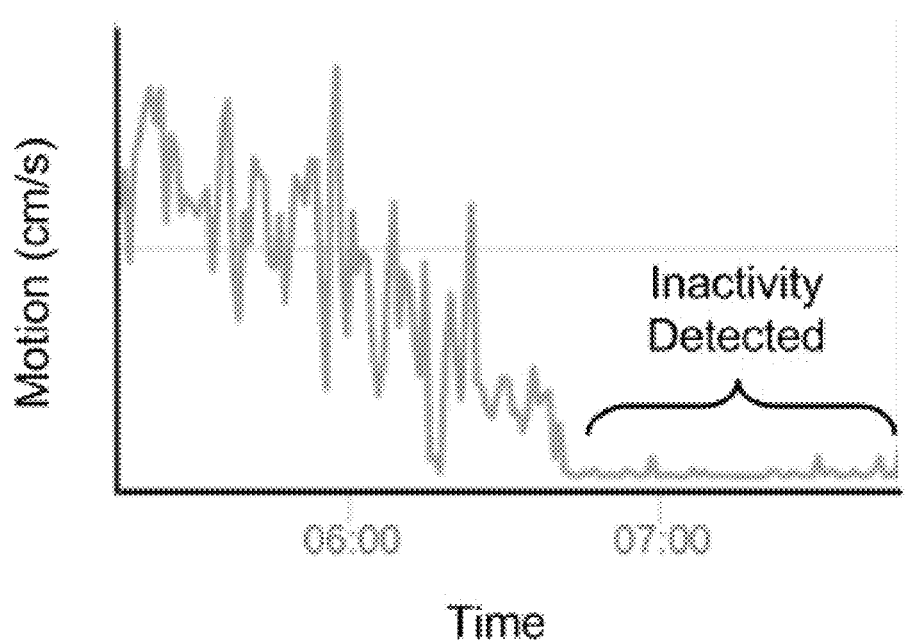
FIG. 9 is a plot of an example of an embodiment of a magnitude of motion in an optical flow over time, where the magnitude remains below a threshold value for a time interval.

Controller 320 may then optionally process the optical flow to determine a temporal region of interest (ROI). The temporal ROI is a segment of time that is selected for further evaluation in order to ultimately determine the respiration rate an experimental animal. The temporal ROI may be selected for a time segment where the maximum magnitude of motion across all spatial cells in the optical flow is below a threshold value for longer than a predefined a time interval (t_inactive). This temporal ROI may be indicate a high likelihood that the experimental animal is in a sleep state or other tranquil state in which the movement of the animal due to respiration can be more readily distinguished from noise. For example, the expansion and contraction of the thorax of a mouse that are caused by respiration generally result in a small change in the magnitude component of the optical flow in comparison to other behaviors like walking or scratching. FIG. 9 is a plot of an example of an embodiment of a magnitude of motion in an optical flow over time, where the magnitude remains below a threshold value for a time interval.

Using a mapping to project one or more of the images onto a plane corresponding to the cage floor, such as in generating a synthesized image, may improve the accuracy of the determination of the temporal ROI by making magnitudes of motion inside the cage substantially invariant to the position of the animal in the cage. The temporal ROI process is optional and may, for example, be included to improve computational efficiency or excluded for the sake of simplicity or to attempt to measure the respiration rate of an animal that is not in a tranquil state.

Figure 11:
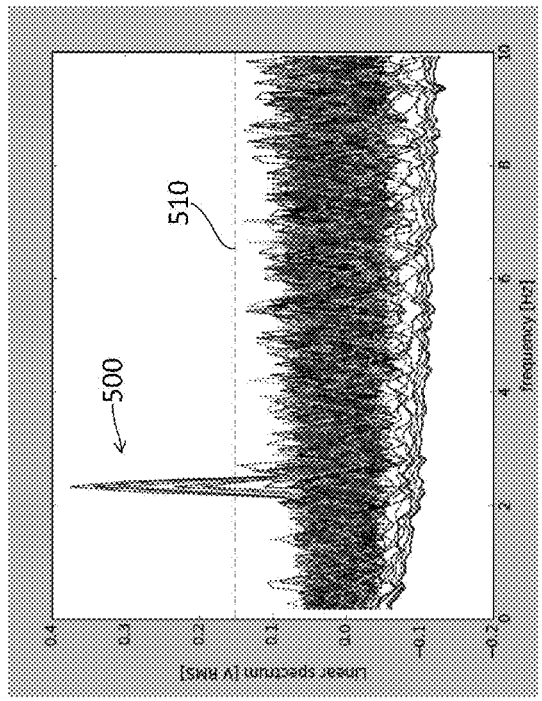
FIG. 11 is a graph of an example of an embodiment of multiple plots, in frequency space, of a direction component of a vector field corresponding to optical flow, where each plot corresponds to one of the spatial cells in FIG. 10.
Figure 10:
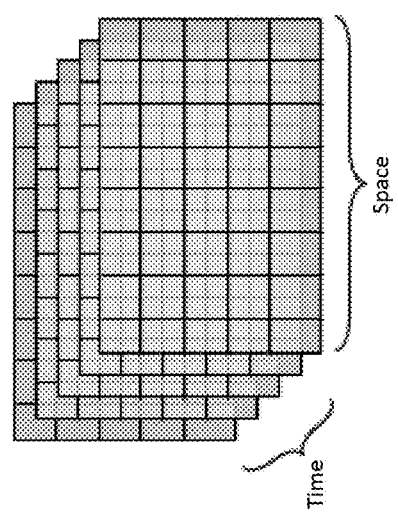
FIG. 10 is a schematic illustration of an example of an embodiment of cells of an image in time and two-dimensional space dimensions.

FIG. 10 is a schematic illustration of an example of an embodiment of cells of an image in time and two-dimensional space dimensions. FIG. 11 is a graph of an example of an embodiment of multiple plots, in frequency space, of a direction component of a vector field corresponding to optical flow, where each plot corresponds to one of the spatial cells in FIG. 10.

Controller 320 may process the optical flow (e.g., between the time planes in FIG. 10) to determine a spatial ROI. In one version, controller 320 evaluates the optical flow within the previously determined temporal ROI to determine, within that temporal ROI, a spatial ROI. The respiration of the animal may create a periodic signal in the direction component of the optical flow within the spatial ROI. The spatial ROI may be determined by selecting cells 500 with an optical flow value (e.g., the direction value) that exceeds a threshold value 510 in frequency space. For example, controller 320 may perform a fast Fourier transform (FFT) independently for each spatial cell across the time dimension. Cells 500 with energy in a given respiration-frequency-range above the threshold 510 are selected.

Figure 12:
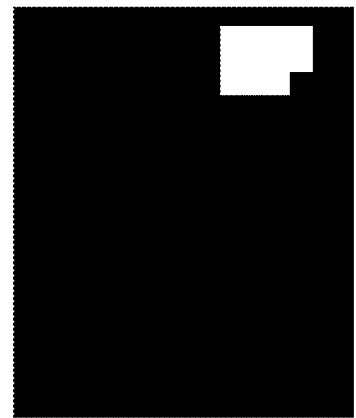
FIG. 12 is a pixelated representation of cells (shown in white) whose corresponding plots in FIG. 11 have a magnitude that exceeds a threshold value within the plotted frequency range.

In one embodiment, the temporal ROI is determined based on the magnitude component of the vector field, and the spectral decomposition for the spatial ROI is performed on the direction component of the vector field. For the sake of illustration, FIG. 12 is a pixelated representation of cells (shown in white) whose corresponding plots 500 in FIG. 11 have a magnitude that exceeds a threshold value 500 within the plotted frequency range. For example, in one illustrative embodiment, the respiration of the animal creates a strong periodic signal in the vector field swinging from 10 degrees to 190 degrees with each cycle, corresponding to inhalation and exhalation, respectively.

Controller 320 may enhance the spatial ROI by reducing or even enlarging the spatial ROI to improve specificity or accuracy. Techniques to enhance the spatial ROI may include, for example, morphological dilation and connected component analysis. For example, cells 500 with an optical flow value that exceeds threshold 510 may correspond to two or more animals. In this case, it may be desired to determine the respiration rate of a single one of the animals with suitable accuracy. To do so, in one example, morphological operations may be applied to the spatial ROI to reduce noise and/or enforce size and/or shape constraints. Connected component analysis may then be used to identify a subregion of each image where the subregion continuously overlaps connected cells that have periodic movement of interest. Connected component analysis may, for example, convert the spatial ROI into a list of polygons where each polygon is a connected component. The enhancement of the spatial ROI is performed at a suitable resolution that may be between the resolution of the cells and the pixel resolution of the underlying image, such as at the pixel resolution of the underlying image.

Within the spatial ROI, the optical-flow signal may be processed according to a space-time volume frequency estimation to subtract, from the signal within the spatial ROI, a noise floor that is common to the regions outside of the spatial ROI. If connected component analysis was applied to the spatial ROI, for example, the spatial ROI being processed according to the space-time volume frequency estimation may be a single connected polygon that corresponds to an individual animal. The average of the FFT for pixels within that spatial ROI may be calculated and associated with the spatial ROI. The optical flow (e.g., the direction component) in that spatial ROI may then be analyzed to find one or more local peaks in frequency space corresponding to the respiration of the animal. The location of the peak represents the estimated respiration rate and the energy of the peak represents the quality of the corresponding space-time region. The intensity of the peak may be used, for example, to generate a confidence level for the measured respiration rate.

Figure 13:
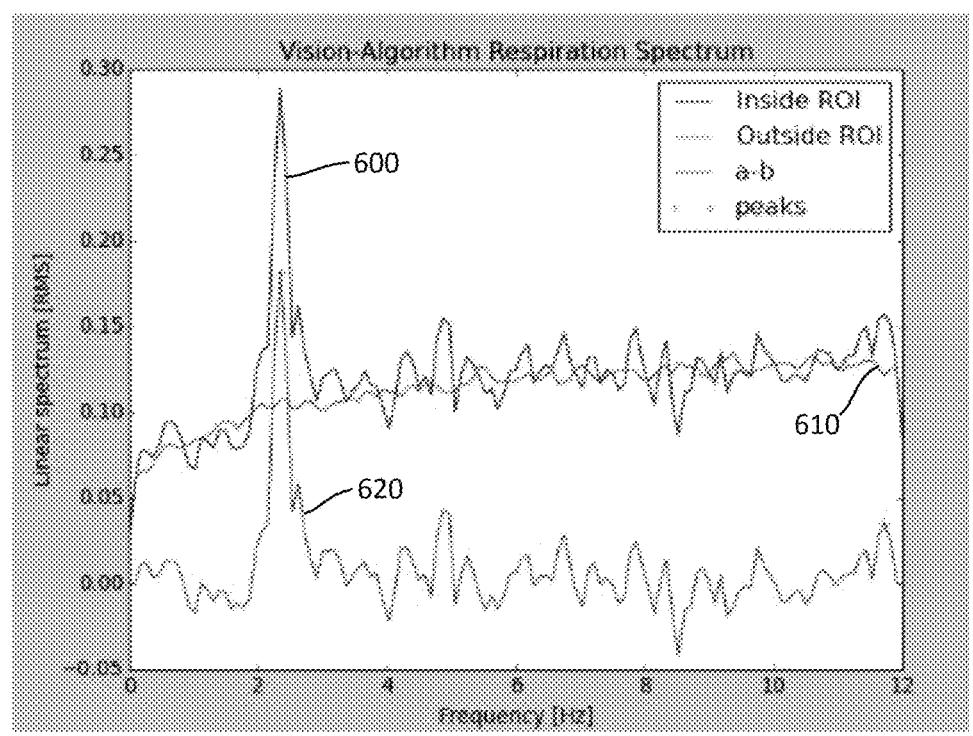
FIG. 13 is a graph of an example of an embodiment of plots, in frequency space, of a direction component of a vector field corresponding to optical flow, where one plot corresponds to a spatial region of interest (ROI), another plot corresponds to the captured video outside of the spatial ROI, and the third plot represents the difference between the first and second plots.

FIG. 13 is a graph of an example of an embodiment of plots, in frequency space, of a direction component of a vector field corresponding to optical flow, where one plot 600 corresponds to a spatial region of interest (ROI), another plot 610 corresponds to the captured video outside of the spatial ROI, and a third plot 620 represents the difference between the first and second plots. Plot 610 contains the respiration signal and a noise floor, plot 620 contains the noise floor without the respiration signal, and plot 630 contains the respiration signal with the noise floor of plot 620 subtracted from it.

Figure 14:
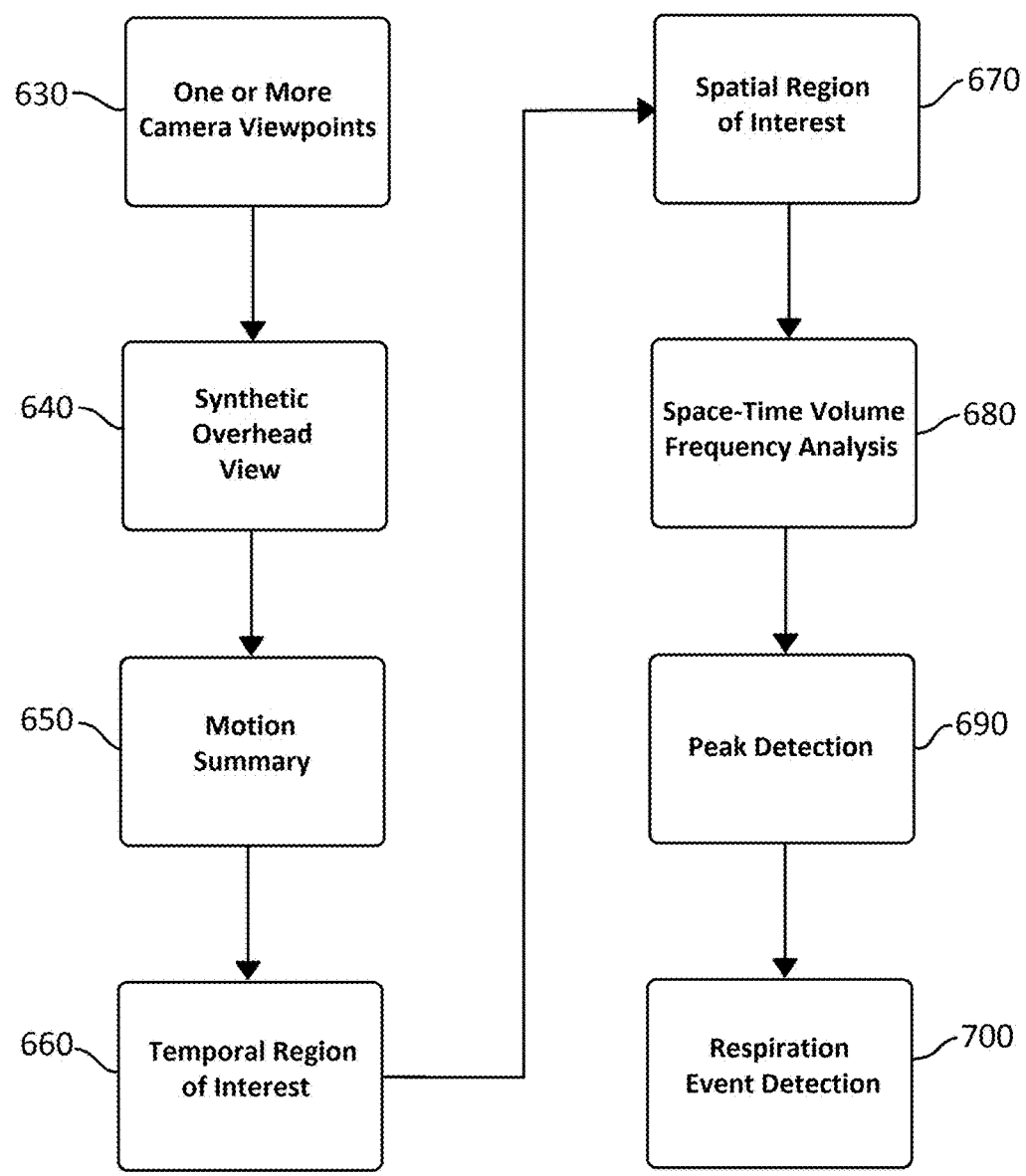
FIG. 14 is a flowchart of an example of an embodiment of a process of measuring a respiration rate of an experimental animal.

FIG. 14 is a flowchart of one version of a process of measuring a respiration rate of an experimental animal. In this embodiment, videos are captured by cameras at one or more locations, representing one or more viewpoints, at step 630. The image frames of the video at each point in time may be synthesized, such as into an overhead view image for each frame, at step 640. The synthesized video may be processed to determine an optical flow, representing a summary of the motion in the video for each point in time, at step 650. From the optical flow, a temporal ROI may be selected during which the experimental animal is estimated to be in a sleep state or other tranquil state in which the movement of the animal due to respiration can be more readily distinguished from noise, at step 660. Within the temporal ROI, a spatial ROI may be selected in which the changes in the video signal due to respiratory movement of the animal predominates, at step 670. Within the spatial ROI, the video signal may be processed according to a space-time volume frequency estimation to subtract, from the signal within the spatial ROI, a noise floor that is common to the regions outside of the spatial ROI, at step 680. The video signal may then be analyzed to find one or more local peaks corresponding to the respiration of the animal, at step 690. From those local peaks, the respiration rate of the animal may be determined, at step 700.

Figure 15:
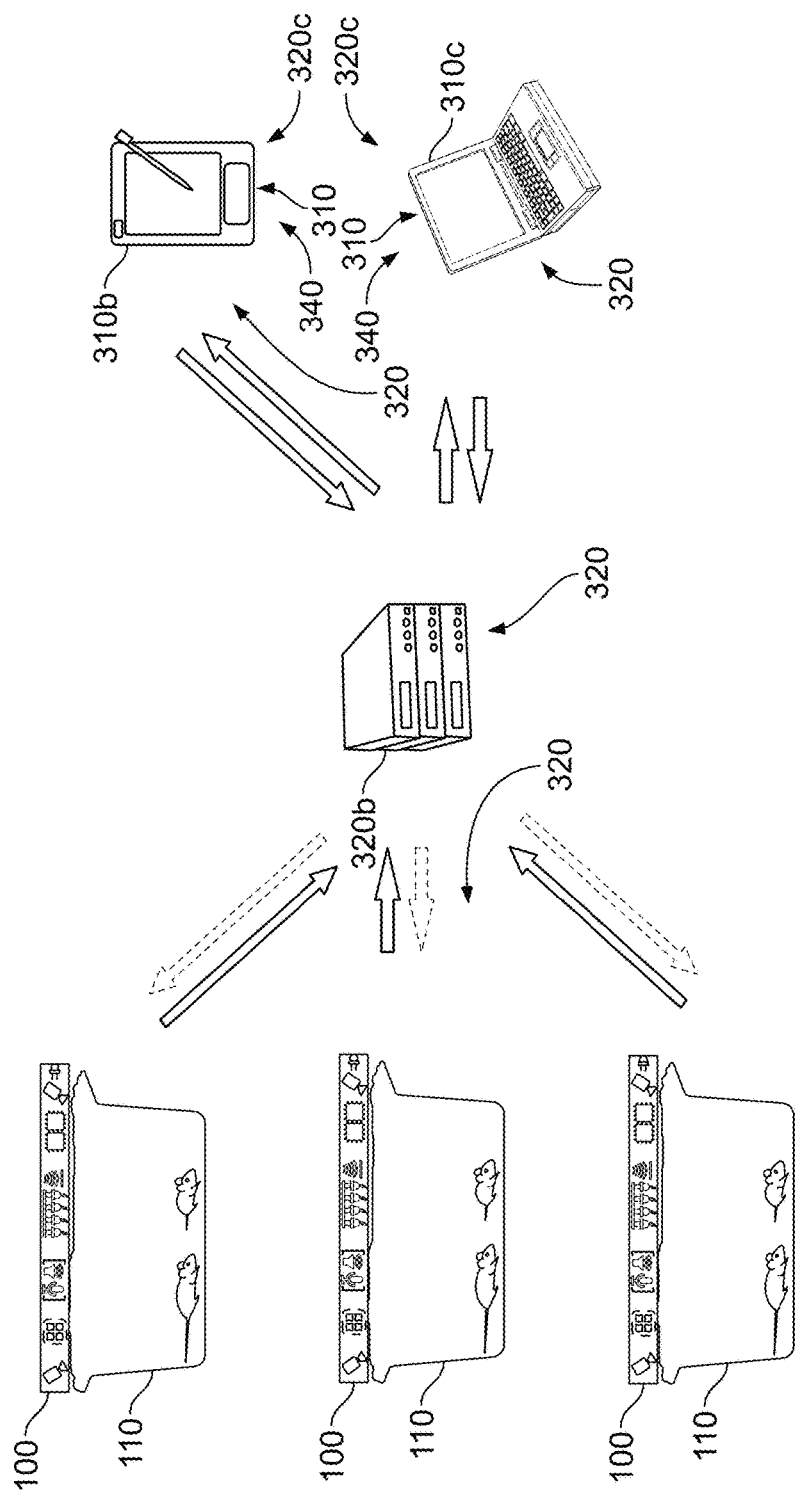
FIG. 15 is a schematic diagram of an example of an embodiment of multiple electronic monitors respectively coupled to cages and interfaced with a human observer.

One or more of user interfaces 310 may be disposed at a location that is not mechanically attached to housing 120 of electronic monitor 100. FIG. 15 illustrates an example of an embodiment of multiple electronic monitors 100 respectively coupled to cages 110 and interfaced with a human observer. In this embodiment, arrayed electronic monitors 100 communicate with an array controller 320*b*, such as a set of servers, that stores and processes the data from sensors 130, 240, 280, detectors 250, weight scales 300, or controller 320*a* of electronic monitors 100. Array controller 320*b* may serve, for example, a rack or multiple racks of electronic monitors 100. Client devices 340 having user interfaces 310*b,c*, and controllers 320*c* which may be referred to as "client devices," may connect to array controller 320*b*. Client devices 340 may include, for example, personal computers (PCs), tablet computers, smartphones, or other suitable devices. The communication between client devices 340 and array controller 320*b* may be bidirectional, such as duplex. Client devices 340 may thereby control and/or request additional information from array controller 320*b*. Communication between electronic monitors 100 and array controller 330 may be unidirectional from electronic monitors 100 to array controller 320*b*. Alternatively, however, this communication may be bidirectional, such as duplex. Client devices 340 or array controller 320*b* may thereby control and/or request additional information from electronic monitors 100.

Figure 16:
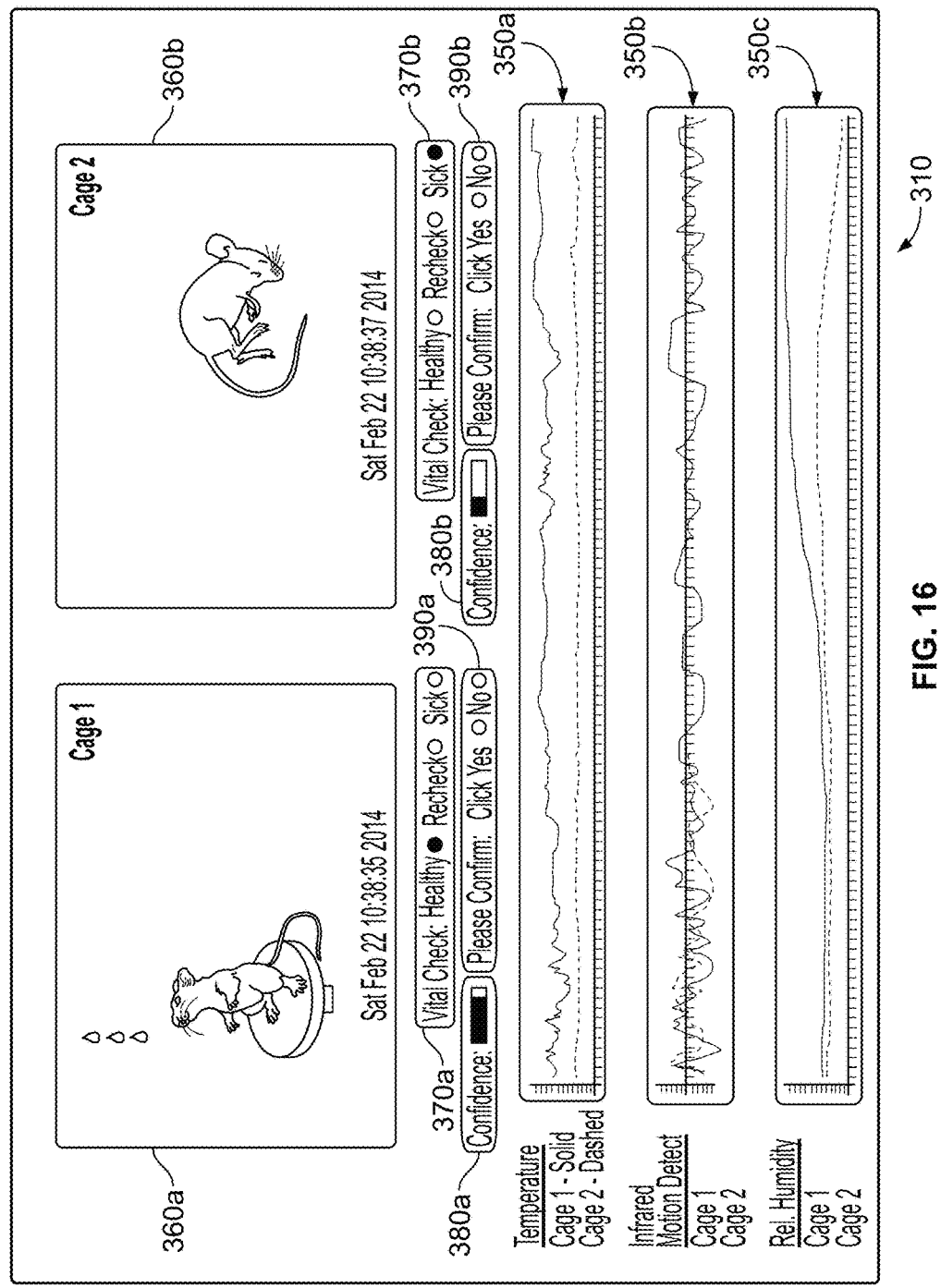
FIG. 16 is an illustration of an example of an embodiment of a display of a user interface of an electronic monitor that is presented for a human observer.

FIG. 16 illustrates an example of an embodiment of a display of a user interface 310 of electronic monitors for a human operator. User interface 310 may be present, for example, on client devices 340. Monitored metrics 350*a-c*, which may include estimated respiration rates of one or more of the experimental animals, may be displayed in a "fused" manner. In the illustrated example, videos 360*a,b* of experimental animals in living spaces in two different cages, or alternatively two regions or views in the same cage, are being observed simultaneously. Furthermore, states 370*a,b* associated with the animals being observed, such as states predicted by controller 320, are displayed. States 370*a,b* may include one or more of the physiological, behavioral, environmental, or other annotations described above, including whether the animal is in a tranquil state such as a sleeping state. Metrics 350*a-c* and states 370*a,b* may be associated with respective confidence levels and input interfaces for the human operator to confirm or reject the predicted states, such as for feedback to a machine learning algorithm being executed by controller 320 to improve the accuracy of future predictions. For example, states 370*a,b* may be associated with confidence levels 380*a,b* and input interfaces 390*a,b*.

Figure 17:
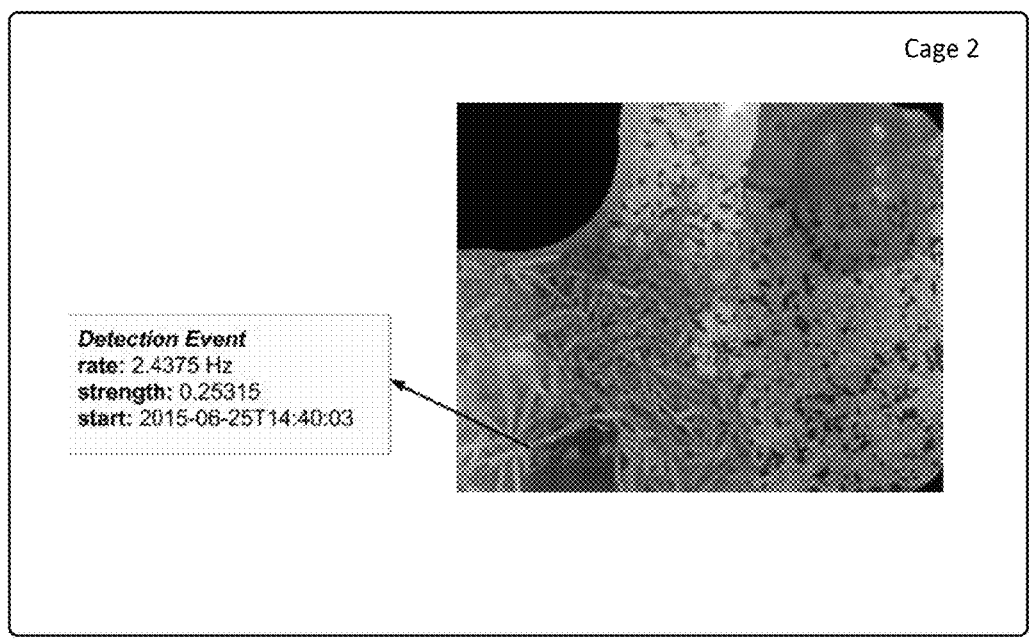
FIG. 17 is an illustration of an example of an embodiment of a grayscale image of a mouse that has annotations describing the detection of a respiration rate at a particular detection start time and a detection strength.

FIG. 17 is an illustration of an example of an embodiment of a grayscale image of a mouse that has annotations describing the detection of a respiration rate at a particular detection start time and a detection strength. The detection strength may correspond to a "confidence" in the accuracy of the estimated respiration rate. This image may be displayed as, for example, one of videos 360*a,b* in FIG. 16. Rich annotations may therefore be overlaid on the video stream indicating to a human user which animal a particular respiration measurements belongs to in a cage with multiple animals. For example, if one animal in a cage containing four animals has labored breathing, the controller may indicate to the user which animal is breathing more slowly than the others.

Returning to FIGS. 1A, 1B, 4, and 15 for the sake of exemplary illustration, the raw data from ambient sensors 130, atmospheric sensors 240, electromagnetic detectors 250, acoustic sensors 280, and/or weight scales 300 of electronic monitors 100 may be processed by controller 320 (which may include one or more of controller 320*a*, array controller 320*b*, and controller 320*c*) to condense the data into reduced-size data sets in one or more sequential stages corresponding to different locations. This may be desirable when there are practical limitations on data throughput. Condensing the data sets may refer to summarizing, compiling, compressing (by either lossy or lossless methods), and/or indexing the data sets. Condensing a video stream, for example, may involve decreasing frame rate or time-lapsing frames from the video stream, providing thumbnails of frames from the video stream, images that each represents a summed series of periodic exposures over time (such as to quickly visualize movement of the animals), or any other suitable method. In one example, a video stream can be compressed according to the H.264 video compression format. Condensing a numerical metric, such as respiration rate, temperature, humidity, or ammonia level, may involve, for example, decreasing resolution of the metric over time where the metric is in a predefined range that is considered normal or uninteresting, and increasing resolution of the metric where the metric is in a range that is deemed interesting.

Controller 320 (which may include one or more of controller 320*a*, array controller 320*b*, controller 320*c*, and servers 320*d*) may also cross-reference data sets from different metrics to improve the quality of the condensed data. In one version, data for one set of metrics is used to condense another metric. For example, if the first set of metrics is within an expected or otherwise "normal" range for a certain timespan, a video stream corresponding to the same timespan may be condensed or even eliminated for viewing at a downstream location. If, however, one of those metrics is outside of a normal range for a particular timespan, or if the set of metrics matches a predetermined trend or signature, a video stream corresponding to that timespan may be transmitted and/or stored in a less condensed form. The less condensed form may involve, for example, lossless compression as opposed to lossy compression, a higher resolution, or a higher frame rate.

Furthermore, controller 320 (or a human supervisor) receiving downstream data may instruct one or more of the ambient sensors 130, atmospheric sensors 240, electromagnetic detectors 250, acoustic sensors 280, and/or weight scales 300 to actually generate higher-resolution raw data for a cage, time period, or physical area of one of cages 110 that is deemed unusually interesting. For example, controller 320 may determine that one of the metrics is currently outside of a normal range, or that a set of metrics are matching a predetermined trend or signature, and instruct one or more of the sensors or detectors described above to turn on or generate data at a higher resolution for a predefined time period. In one example, an anomalous metric may trigger controller 320 to turn on video cameras to record the experimental animals in a cage at high resolution and continuously for a predefined timespan. In another example, one or more metrics are used to determine if an experimental animal is in a sleeping or otherwise tranquil state and, when the animal is determined to be in that tranquil state, turn on video cameras at a high resolution to determine a respiration rate of the animal.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the appended claims. It is also to be understood that the terminology used herein is for the purpose of describing particular aspects only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order that is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein.

In this specification, various preferred embodiments have been described with reference to the accompanying drawings. It will be apparent, however, that various other modifications and changes may be made thereto and additional embodiments may be implemented without departing from the broader scope of the claims that follow. The specification and drawings are accordingly to be regarded in an illustrative rather than restrictive sense.

We claim:

1. A respiration rate detector for determining a rate of respiration of an experimental animal, the respiration rate detector comprising:
   one or more optical detectors to observe an experimental animal and generate a video signal relating to the experimental animal; and
   a controller to:
   process the video signal to determine an optical flow of the video signal and generate an optical-flow signal,
   process the optical-flow signal to determine a spatial region-of-interest of the optical-flow signal, the spatial region-of-interest comprising one or more spatial cells of the optical-flow signal, wherein processing the optical-flow signal to determine the spatial region-of-interest comprises evaluating the optical-flow signal in frequency space and selecting one or more spatial cells having a value in frequency space that exceeds a threshold value,
   analyze the optical-flow signal within the spatial region-of-interest to determine the respiration rate of the experimental animal based on a detected repetitive movement of the experimental animal, and
   display the determined respiration rate to an operator,
   wherein the respiration rate is detected without requiring physical contact with the experimental animal.

2. The respiration rate detector of claim 1, wherein the controller is adapted to encode the optical flow as two two-dimensional floating-point matrices.

3. The respiration rate detector of claim 1, wherein the controller is adapted to determine the spatial region-of-interest such that the spatial cells of the spatial region-of-interest have periodic movement of at least a threshold magnitude within a predefined frequency range.

4. The respiration rate detector of claim 3, wherein the controller is adapted to enhance the spatial region-of-interest by connected component analysis to identify a continuous subregion of an image.

5. The respiration rate detector of claim 3, wherein the controller is adapted to subtract, from the signal within the determined spatial region-of-interest, a noise floor obtained from spatial cells that are outside of the determined set.

6. The respiration rate detector of claim 1, wherein the controller is adapted to define spatial cells that have a size of from $0.001$ cm$^2$ to $400$ cm$^2$.

7. The respiration rate detector of claim 1, wherein the controller is adapted to determine a temporal region-of-interest of the optical-flow signal, during which the experimental animal is estimated to be in a tranquil state.

8. The respiration rate detector of claim 1, wherein the controller is adapted to identify a local peak of periodic movement within a preselected frequency range corresponding to a range of possible expected respiration rates of the experimental animal.

9. The respiration rate detector of claim 1, wherein the controller is adapted to synthesize image frames of the video from different camera perspectives and generate an optical-flow signal based on the synthesized video.

10. The respiration rate detector of claim 1, wherein the controller is adapted to compute the optical flow from the video signal by a correlation method.

11. The respiration rate detector of claim 1, wherein determining the spatial region-of-interest comprises one or more of reducing and enlarging the spatial region-of-interest before analyzing the optical-flow signal within the reduced and/or enlarged spatial region-of-interest to determine the respiration rate.

12. The respiration rate detector of claim 1, wherein determining the spatial region-of-interest comprises determining a spatial region-of-interest that corresponds to two or more experimental animals, and wherein analyzing the optical-flow signal within the spatial region-of-interest comprises analyzing the optical-flow signal to determine the respiration rate of a single one of the two or more experimental animals based on a detected repetitive movement of that experimental animal.

13. The respiration rate detector of claim 1, wherein the controller is further adapted to determine a confidence level in relation to the determined respiration rate and to display the confidence level to the operator.

14. A method of determining a rate of respiration of an experimental animal, the method comprising:
- observing an experimental animal with one or more optical detectors to generate a video signal;
- processing the video signal to determine an optical flow of the video signal and generate an optical-flow signal;
- processing the optical-flow signal to determine a spatial region-of-interest of the optical-flow signal, the spatial region-of-interest comprising one or more spatial cells of the optical-flow signal, wherein processing the optical-flow signal to determine the spatial region-of-interest comprises evaluating the optical-flow signal in frequency space and selecting one or more spatial cells having a value in frequency space that exceeds a threshold value;
- analyzing the optical-flow signal to determine the respiration rate of the experimental animal based on a detected repetitive movement of the experimental animal; and
- displaying the determined respiration rate to an operator, wherein the respiration rate is detected without requiring physical contact with the experimental animal.

15. The method of claim 14, wherein processing the video signal comprises encoding the optical flow as two two-dimensional floating-point matrices.

16. The method of claim 14, wherein analyzing the optical-flow signal comprises determining the spatial region-of-interest such that the spatial cells of the spatial region-of-interest have periodic movement of at least a threshold magnitude within a predefined frequency range.

17. The method of claim 16, wherein analyzing the optical-flow signal comprises enhancing the spatial region-of-interest by connected component analysis to identify a continuous subregion of an image.

18. The method of claim 16, wherein analyzing the optical-flow signal comprises subtracting, from the signal within the determined spatial region-of-interest, a noise floor obtained from spatial cells that are outside of the determined set.

19. The method of claim 14, wherein processing the video signal comprises defining spatial cells that have a size of from 0.001 $cm^2$ to 400 $cm^2$.

20. The method of claim 14, wherein analyzing the optical-flow signal comprises selecting a temporal region-of-interest during which the experimental animal is estimated to be in a tranquil state.

21. The method of claim 14, wherein analyzing the optical-flow signal comprises identifying a local peak of periodic movement within a preselected frequency range corresponding to a range of possible expected respiration rates of the experimental animal.

22. The method of claim 14, wherein processing the video signal comprises synthesizing image frames of the video from different camera perspectives and generating an optical-flow signal based on the synthesized video.

23. The method of claim 14, wherein processing the video signal comprises computing the optical flow from the video signal by a correlation method.

24. The method of claim 14, wherein processing the optical-flow signal to determine the spatial region-of-interest comprises one or more of reducing and enlarging the spatial region-of-interest before analyzing the optical-flow signal within the reduced and/or enlarged spatial region-of-interest to determine the respiration rate.

25. The method of claim 14, wherein determining the spatial region-of-interest comprises determining a spatial region-of-interest that corresponds to two or more experimental animals, and wherein analyzing the optical-flow signal comprises analyzing the optical-flow signal to determine the respiration rate of a single one of the two or more experimental animals based on a detected repetitive movement of that experimental animal.

26. The method of claim 14, further comprising determining a confidence level in relation to the determined respiration rate and displaying the confidence level to the operator.

* * * * *